United States Patent [19]

Sprecker

[11] 4,123,469

[45] Oct. 31, 1978

[54] PROCESS FOR PRODUCTION OF BICYCLIC COMPOUNDS

[75] Inventor: Mark A. Sprecker, Sea Bright, N.J.

[73] Assignee: International Flavors & Fragrances Inc., New York, N.Y.

[21] Appl. No.: 811,616

[22] Filed: Jun. 30, 1977

[51] Int. Cl.² .............................................. C11B 9/00
[52] U.S. Cl. ............................ 260/668 F; 260/668 B; 252/522
[58] Field of Search ...................... 260/668 B, 668 F; 252/522

[56] References Cited

U.S. PATENT DOCUMENTS

| | | | |
|---|---|---|---|
| 2,897,237 | 7/1959 | Carpenter | 260/668 F |
| 3,152,192 | 10/1964 | Wood et al. | 260/668 F |
| 3,360,530 | 12/1967 | Heeringa et al. | 252/522 |
| 3,532,719 | 10/1970 | Theimer | 252/522 |
| 3,910,853 | 10/1975 | Kulka | 252/522 |

OTHER PUBLICATIONS

I. P. Labunski et al., Chem. Ab. 46:5022(b), 1952.

*Primary Examiner*—Veronica O'Keefe
*Attorney, Agent, or Firm*—Arthur L. Liberman; Franklin D. Wolffe; Harold Haid

[57] ABSTRACT

Described is a process for producing bicyclic compounds having the generic structure:

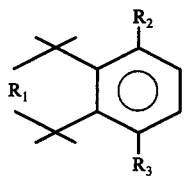

wherein $R_1$ is one of the moieties:

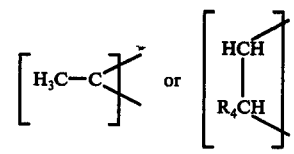

and wherein $R_2$, $R_3$ and $R_4$ are the same or different and each represents hydrogen, methyl or ethyl comprising the step of reacting a tricyclic compound having the structure:

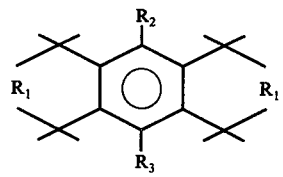

with a benzene derivative having the structure:

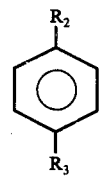

according to the reaction:

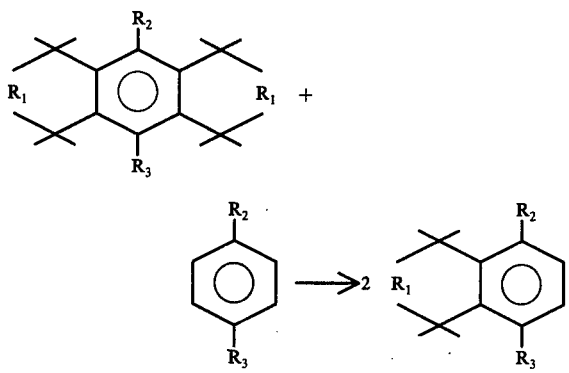

in the presence of an aluminum chloride catalyst.

4 Claims, 5 Drawing Figures

FIG.2

GLC PROFILE, EXAMPLE I
25° REACTION AFTER FOUR HOURS.

FIG.3

GLC PROFILE, EXAMPLE II
REACTION PRODUCT AFTER
CATALYST ADDITION.

FIG.4

GLC PROFILE, EXAMPLE II REACTION PRODUCT AFTER ONE HOUR AT 40°C.

FIG.5

GLC PROFILE, EXAMPLE II REACTION PRODUCT AFTER THREE HOURS AT 40° C.

PROCESS FOR PRODUCTION OF BICYCLIC COMPOUNDS

BACKGROUND OF THE INVENTION

The production of isochromans is disclosed in the prior art and certain novel isochromans have been disclosed with an outstanding musk fragrance. Such isochromans especially adapted for perfumery by virtue of their fragrance properties were disclosed in Heeringa and Beets, U.S. Pat. No. 3,360,530, issued on Dec. 26, 1967 as well as U.S. Pat. No. 3,978,090, issued on Aug. 31, 1976 to Sanders and Michael. Furthermore, the production of cyclic nitriles has been shown in the prior art and certain bicyclic nitriles have recently been disclosed with an outstanding musk fragrance. Such bicyclic nitriles especially adapted for perfumery by virtue of their fragrance properties have been disclosed in Kulka, U.S. Pat. No. 3,910,853, issued on Oct. 7, 1975. The reaction route for producing these nitriles is set forth, inter alia in U.S. Pat. No. 3,910,853 at Column 2 and at Column 3 as follows:

"in which R is methyl or ethyl." (R can also be hydrogen).

"The resulting 1,1,4,4-tetramethyl-6-alkyl-1,2,3,4-tetranydronaphthalene is chloromethylated with paraformaldehyde and hydrochloric acid in the presence of glacial acetic acid and phosphoric acid to produce 1,1,4,4-tetramethyl-6-alkyl-7-chloromethyl-tetrahydronaphthalene in accordance with the following reaction:

The resulting 1,1,4,4-tetramethyl-6-alkyl-7-chloromethyl-tetrahydronapthalene is then reacted with 2-nitropropane and sodium methoxide in methanol solution. An exothermic reaction takes place. After the completion of the reaction, water and benzene are added. The resulting mixture is then separated into an organic part and an aqueous part. The organic part is washed successively with a 5% sodium hydroxide solution followed by two washings with water. The benzene is removed by distillation and the reaction product solidified. The resulting product may be recrystallized from a suitable solvent such as methanol. The reaction which takes place is as follows:

The 1,1,4,4-tetramethyl-6-alkyl-7-formyl-tetrahydronaphthlene formed is reacted with hydrolxyamine hydrochloride dissolved in water. The reaction mixture is agitated for a period of about 5 minutes, after which a solution of sodium hydroxide is added. After agitation for about 3 hours, the reaction mixture is cooled by the addition of shaved ice. The reaction mixture is then saturated with carbon dioxide by the gradual addition of solid carbon dioxide. The mixture is permitted to stand for several hours. The reaction which takes place is as follows:

The resulting 1,1,4,4-tetramethyl-6-alkyl-7-aldoxime tetrahydronaphthalene is reacted with acetic anhydride. The mixture is agitated and gradually heated over a period of about 15 minutes, to about 123° C. It is then refluxed for 1 hour. The reaction mixture is then permitted to cool to room temperature and a mixture of water and benzene is added. The reaction product in benzene solution is then washed successively 3 times with water, twice with aqueous sodium carbonate solution, once with aqueous sodium bicarbonate solution and finally with water. The solvent is removed by distillation and the product recrystallized by a suitable solvent such as methanol. The reaction which takes place is as follows:

The process for producing isochromans of U.S. Pat. No. 3,978,090 having the structure:

"wherein $R_1$ and $R_2$ are each (i) separately selected from the group consisting of hydrogen, lower alkoxyl, lower alkyl, and, (ii) taken together, selected from the group consisting of benzo, cyclopentano, cyclohexano, naphtho, monoalkyl cyclopentano, polyalkyl cyclopentano, monoalkyl cyclohexano and polyalkyl cyclohexano, and $R_3$ and $R_4$ are the same or different and are selected from the group consisting of hydrogen and lower alkyl comprises the steps of intimately admixing:

A. An alkanol having the structure:

B. An acetal having the structure:

(wherein $R_5$ and $R_6$ are each 2-propyl);

C. A protonic acid selected from the group consisting of p-toluene sulfonic acid and phosphoric acid; and D. An azeotroping agent selected from the group consisting of n-hexane, cyclohexane, methyl cyclohexane, benzene and toluene; and simultaneously (i) heating the resulting mixture for a period of time whereby a substantial amount of the isochroman having the above structure is formed while (ii) azeotropically removing water of reaction with the azeotroping agent."

A specific example of one of the reactions of U.S. Pat. No. 3,978,090 is the reaction of the iso-propylalcohol acetal of formaldehyde with 2-(1', 1', 2', 3', 3'-pentamethylindan-5'yl)-propanol-1 which yields 6-oxa-1,1,2,3,3,8-hexamethyl-2,3,5,6,7,8-hexahydro-1H-benz(-f)indene as follows:

Another example of this process is the formation of 2-oxa-4,5,5,8,8,-pentamethyl-1,2,3,4,5,6,7,8-octahydroanthracene as follows:

Alternative routes are also available for the production of isochromans such as those set forth in U.S. Pat. No. 3,360,530 and one of the most straightforward of these routes is the treatment of a Friedel Crafts reactant with an alkaline oxide under Friedel Crafts conditions to form an aryl alkanol. The aryl alkanol is then isolated and thereafter reacted with formaldehyde to cyclialkylate the alcohol.

The efficiency of the aforesaid multistage processes leaves much to be desired because of yield impairment due to the large amount of working required.

In addition, U.S. Pat. No. 3,532,719 sets forth a process for producing such isochromans, which process at the time of patent application, solved a number of these problems of the processes set forth in U.S. Pat. No. 3,360,530. U.S. Pat. No. 3,532,719 provided a more simplified more economical process for producing isochromans which comprises reacting a Friedel Crafts reactant with alkaline oxide in the presence of aluminum chloride to form an aryl alkanol, partially deactivating the aluminum chloride after formation of the aryl alkanol and cyclialkylating the aryl alkanol with formaldehyde in the presence of the partially deactivated aluminum chloride to form the isochroman. The disadvantage of such procedures for the preparation of isochromans is in the first step wherein the Friedel Crafts reactant is formed (e.g. the bicyclic hydrocarbon) and in the second step wherein chloromethylmethylethers may be involved which have been reported to be health hazards accordingly requiring special precautions when handling. The preparation and use of such chloromethylmethylethers and the use of aluminum chloride complexes give rise to the release of hydrogen chloride vapors and formation of aqueous hydrogen chloride solutions require the use of more expensive glass lined vessels due to the more corrosive mixtures in the reaction.

The question of dealkalytion, transakalytion and reversability in the Friedel Crafts reaction is extensively discussed in "Friedel Crafts and Related Reactions", Volume 1 edited by G. A. Olah, Interscience 1963 at pages 36 and 37 wherein it is stated:

"It has long been known that the action of aluminum chloride is not restricted to the introduction of alkyl groups into aromatics. It can also be used to remove alkyl groups from alkylbenzenes (dealkylation) . . . Therefore it has often been stated that Friedel Crafts alkylations are reversible . . . Hexamethylbenzene heated at 190°–200° with aluminum chloride gives methyl chloride and a mixture of hydrocarbons: pentamethylbenzene, durene, isodurene, trimethylbenzenes, xylenes, and small amounts of benzene and toluene. If a stream of dry hydrogen chloride is passed through the mixture the dealkylation is easier and more complete. When methylbenzenes having 1–4 methyl groups are heated with aluminum chloride, dealkylation and alkylation proceed together so that the product is a mixture of hydrocarbons, some with fewer and some with more alkyl groups than the original alkyl benzene. Thus mesitylene yields xylenes and durenes, as well as smaller amounts of toluene and benzene. Alkyl groups containing two or more carbon atoms are readily transferred from one position to another and from one benzene nucleus to another (intra- and intermolecular isomerization). Polyethylbenzenes react with benzene to give ethylbenzene. Isopropyl and t-butyl groups are still more readily transferred and one alkyl group can displace another."

The Olah publication is not considered to disclose either explicitly or implicitly the reaction of my invention.

Although condensation of ditertiary glycols with benzene is disclosed at Chem. Abs. (1952) 5022(b) (Abstract of Labunskii and Tsukervanik, Doklady, Akad. Nauk S.S.R. 80 369–72), the instant disproportionation reaction is not so disclosed therein. The Chem. Abstract reference states:

"$C_6H_6$ concenses with $(Me_2C(OH))_2$ only if 2–2.5 moles $AlCl_3$ are used at 80°, yielding 8% 1,1,2-trimethyl-indan and some 50% $Me_2CAc$. $CH_2(CMe_2OH)_2$ with 1.5 moles $AlCl_3$ at 50°–70° yields 52.5% 1,1,3,3-tetramethyl-indan and 18% 1,2,3,5,6,7-hexahydro-1,1,3,3,5,5,7,7-octamethyl-indacene, m. 214°, while 2,5-dimethyl-2,5-hexanediol similarly gives 57.3% 1,1,4,4-tetramethyl-1,2,3,4-tetrahydronaphthalene and 1,1,4,4,5,5,8,8-octamethyl-1,2,3,4,5,6,7,8-octahydroanthracene (20%). Reaction with $MeCH-(OH)CH_2$-$C(OH)Me_2$ with 1.5 moles $AlCl_3$ at 50°–60° gave 20% $Me_2CPhCH_2CH(OH)Me$ and 25% 1,1,3-trimethyl-indan. $Me_2C(OH)CH_2COMe$ with 2 moles $AlCl_3$ at 20° gave 61% $PhCH_2CHMeCH_2COMe$ and a little unknown product, m. 127°. The mechanism is probably analogous to that given for ROH (Byull. Sredneaziat. Gosudarst. Univ. No. 25, 45(1947), with additional possibility of intermediate formation of oxido structures."

In Chem. Abstracts 163,834d, Volume 77, 1972 (Abstract of Badr and Zarif, J. Appl. Chem. Biotechnol. 1972, 22(9), 967-72) rearrangement of bicyclic aromatics using phenol and naphthol is disclosed thusly:

"Isomerization of alkyl naphthalenes by anhydrous sulfonic acids or Friedel-Crafts and Lewis Acid catalysts was studied, where alkyl groups underwent rearrangement during the isomerization. Isomerization of benzylnaphthalenes, in presence of phenol and naphthols, resulted in the alkylation of the solvents, giving benzylphenols, benzyl naphthols and the normal products of isomerization."

Chem. Abstracts 59:3847h (Abstract of Shadmanov (Belinskii Ped. Inst. Tashkent) states that condensation of 2,5-dimethyl-2,5-dichlorohexane (I) with $C_6H_6$ gives 1,1,4,4-tetramethyltetrahydronaphthalene (II) and 1,1,4,4,5,5,8,8-octamethyloctahydroanthracene (III). With use of the molar ratio $C_6H_6$—I—$AlCl_3$ - 45.8:1:0.1 and temp. 76°–80° for 24 hours only II (85%), $b_3$ 98°–100°, $n_D^{20}$ = 1.5218, d=0.9328 was obtained. Working with temp. 20°–2° for 72 hours only III (60–78%) b. 218°–20° was obtained.

The aforementioned teachings do not however, imply that the disproportionation reaction of the instant invention can take place under the stated conditions.

Preparation of 1,1,4,4-tetramethyl-1,2,3,4-tetrahydronaphthalene using aluminum chloride as a catalyst is disclosed in Bruson and Kroeger, Volume 62, J. Am. Chem. Soc. January 1940, Pages 36–44 (Title: "Cycli-Alkylation of Aromatic Compounds by the Friedel and Crafts Reaction"). However, the disproportionation reaction of the instant invention is not disclosed by Bruson and Kroeger.

THE INVENTION

The present invention provides a simple economic and efficient process for producing mono-cyclialkylated aromatic compounds which are precursors for such materials as isochromans or cyclialkylated aromatic nitriles. The process of my invention involves carrying out the disproportionation reaction of an aromatic compound with a bicyclialkylated aromatic compound in the presence of an aluminum chloride catalyst whereby when one mole of the aromatic compound is reacted with one mole of the bicyclialkylated aromatic compound, two moles of the mono-cyclialkylated aromatic compound are produced as follows:

+ wherein $R_1$ is selected from the group consisting of the moieties:

and $R_2$, $R_3$ and $R_4$ are the same or different and each represents hydrogen, methyl or ethyl.

The reaction may be either carried out (i) in situ after the original "monocyclialkylation" reaction is carried out and the bicyclialkylated product is formed together with the desired monocyclialkylated product, or (ii) it may be carried out on the neat bicyclialkylated aromatic compound. In both cases, a specified range of quantities of aluminum chloride catalyst and a specified range of ratios of aromatic compound: bicyclialkylated compound should be used, as more particularly described herein below.

Thus, when the reaction is carried out "in situ" the initial monocyclialkylation is carried out under standard known "prior art" conditions with the exception that the aromatic compound is in molar excess with respect to the cyclialkylation reagent. The "in situ" reaction is carried out initially at a temperature in the range of from 15 up to 25° C. When all of the ditertiary alcohol (or "diol") is reacted, for example when carrying out the reaction:

the reaction mass is warmed to a temperature in the range of from about 25° C up to the reflux temperature of the reaction mass, e.g. about 80° C, whereupon any bicyclialkylated aromatic compound is subjected to a disproportionation reaction whereby substantially all monocyclialkylated aromatic compound is produced, for example according to the reaction:

or the reaction:

In "in situ" reaction is carried out using a large molar excess of aromatic compound (which is recoverable) in the presence of an aluminum chloride catalyst (which is critical to the process). The mole ratio or aromatic compound: diol is in the range of from about 15:1 up to about 50:1 with a preferred ratio of from 20:1 up to 35:1. If the mole ratio is below about 15:1 then solubility problems exist. The mole ratio range of diol compound: aluminum chloride is from about 2:1 up to about 5:1 with a preferred mole ratio of 2.1:1.

In the case where the reaction of my invention is carried out by means of reacting the aromatic compound with the neat bicyclialkylated aromatic compound according to the reaction:

wherein $R_1$ is selected from group consisting of the moieties:

and $R_2$, $R_3$ and $R_4$ are the same or different and each represents hydrogen, methyl or ethyl, a large molar excess of aromatic compound (which is recoverable) is used and the reaction is carried out in the presence of aluminum chloride at a temperature in the range of from about 40° C up to reflux temperature (e.g. 80° C) and for a period of time of from about 1 hour up to about 10 hours. The mole ratio of bicyclialkylated aromatic compound; aluminum chloride catalyst may vary from about 1:100 to about 1:0.25 with a preferred ratio of bicyclialkylated aromatic compound: aluminum chloride catalyst being about 1:2. The mole ratio of aromatic compound: bicyclialkylated aromatic compound in this reaction may vary from about 2:1 to about 40:1 with a preferred mole ratio range of from about 10:1 to about 15:1.

The resulting monocyclialkylated aromatic compound can be further reacted "as is" or they can be purified and then further reacted with, for example acylation reagents such as acetyl chloride or acetic anhydride or with the following reagents, in sequence, in order to add a C≡N moiety to the aryl ring:

1. A chloromethylation reagent such as para formaldehyde and hydrochloric acid thereby forming a chloromethyl substituent on the ring;
2. Nitropropane in order to transform the chloromethyl group into a carboxaldehyde group;
3. Hydroxylamine in order to transform the carboxaldehyde group into a alkoxime group;
4. Acetic anhydride in order to transform the aldoxime group into a C≡N group.

Thus the following sequence of reactions can be performed on the products of our invention, for example:

In addition, as stated in the "background" section of this application, the cyclialkylated aromatic compounds can be transformed into isochromans (useful in perfumery) according to the following reactions, using epoxides followed by cyclization of the resulting alcohol with formaldehyde:

The following examples I - IV are given to illustrate embodiments of my invention as it is presently preferred to practice it. It will be understood that these examples are illustrative and the invention is not to be considered as restricted thereto except as indicated in the appended claims.

Example V is illustrative of the prior art.

EXAMPLE I

PREPARATION OF 1,1,4,4-TETRAMETHYLTETRAHYDRONAPHTHALENE

Reaction:

Into a 12 liter reaction flask equipped with air driven stirrer, large bulb reflux condenser leading into 1 liter Erlenmeyer flask and cooling bath is placed:
1. 2,5-dimethyl-hexane-2,5-diol — 511 grams (3.5 moles)
2. Benzene anhydrous — 7000 grams (89 moles)

Figure 1:
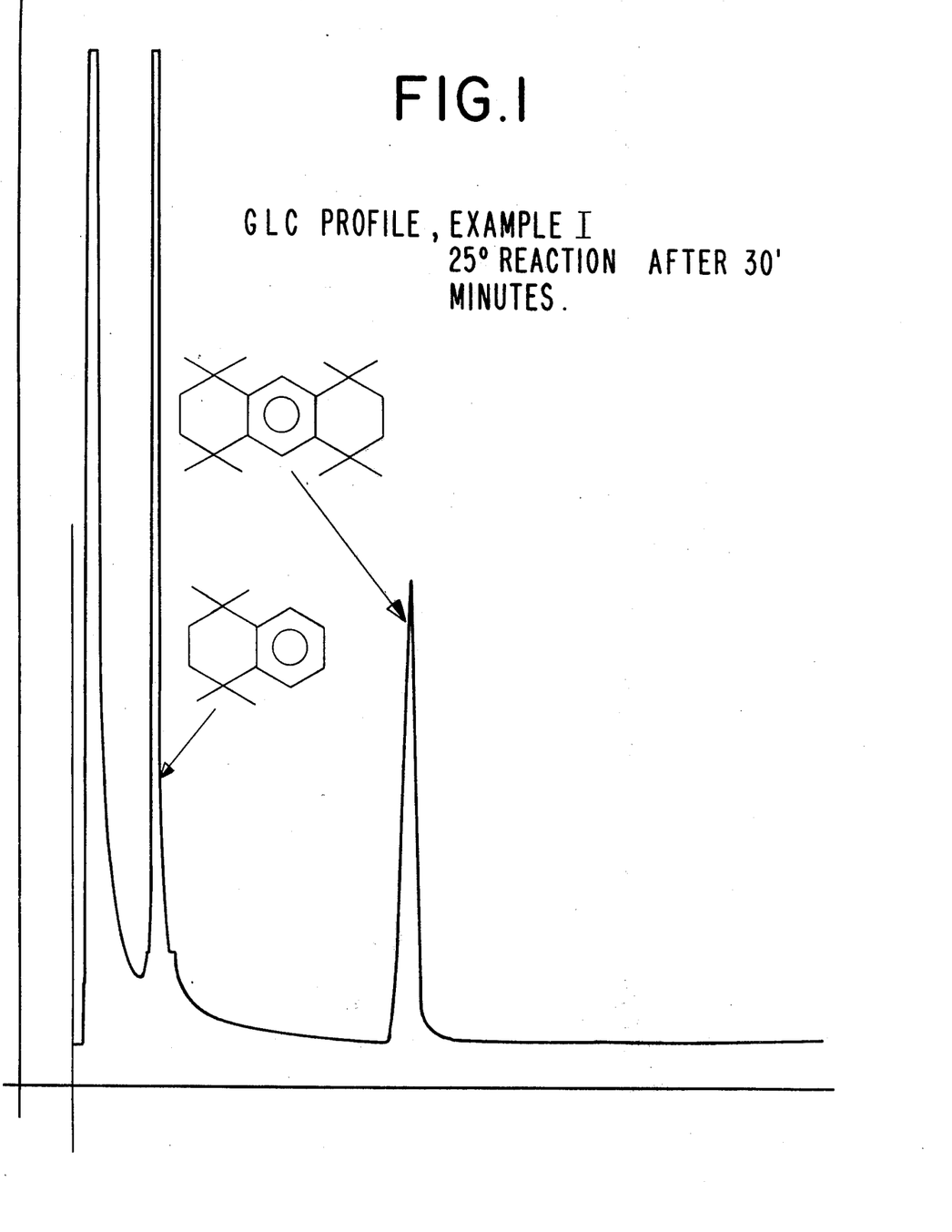
FIG. 1 represents the GLC profile of the reaction product produced according to Example I, 30 minutes after addition of Lewis acid catalyst.
Figure 2:
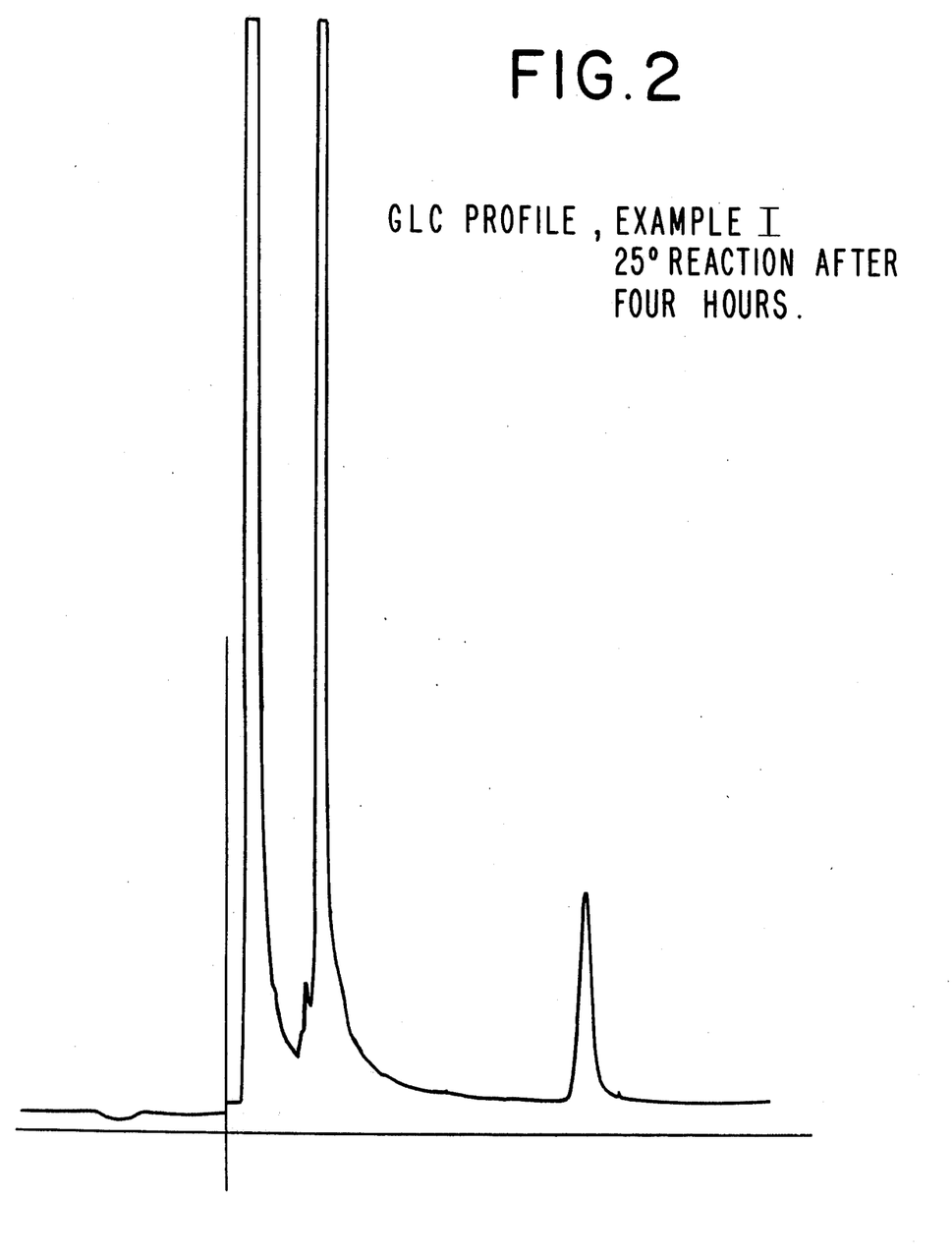
FIG. 2 represents the GLC profile of the reaction product produced according to Example I, 4 hours after addition of Lewis acid catalyst.

The resulting mixture is heated to 50° C in order to dissolve all of the dimethylhexanediol. When all of the dimethyl hexanediol is dissolved the reaction mass is cooled to 25° C. 934.5 grams (7 moles) of anhydrous aluminum chloride is then added slowly over a period of 1 hour to the reaction mass while stirring while maintaining the temperature of the reaction mass at between 20° and 25° C. The reaction mass is stirred while maintaining same at 23° - 27° C over a period of 4 hours. At the end of the 4 hour period 2.5 liters of water is added to the reaction mass and the organic phase is separated. The organic phase is then washed with 1 liter of water followed by 100 ml of 10% sodium hydroxide solution. The solvent is then removed by distillation at atmospheric pressure. Distillation of the remaining oil at 85°–100° C (5-10 min.) yields 511 grams of 1,1,4,4-tetramethyltetrahydronaphthalene (theoretical yield 693 grams) FIG. 1 illustrates the aluminum chloride is added thereto (conditions: ⅛ inch × 10 feet 10% SE-30 column operated at 220° C, isothermal). FIG. 2 sets forth the GLC profile of the reaction mass four hours after all of the aluminum chloride is added thereto. Conditions: ⅛ inch × 10 feet 10% SE-30 column operated at 220° C, isothermal).

EXAMPLE II

PREPARATION OF 1,1,4,4-TETRAMETHYLTETRAHYDRONAPHTHALENE

Reaction:

Into a 12 liter reaction flask equipped with stirrer, thermometer, reflux condenser, heating mantle, cooling bath and Gouch tubing is placed:
1. 596.5 grams (3.9 moles) of 2,5-dimethylhexane-2,5-diol
2. 7200 grams (91 moles) of benzene

Figure 3:
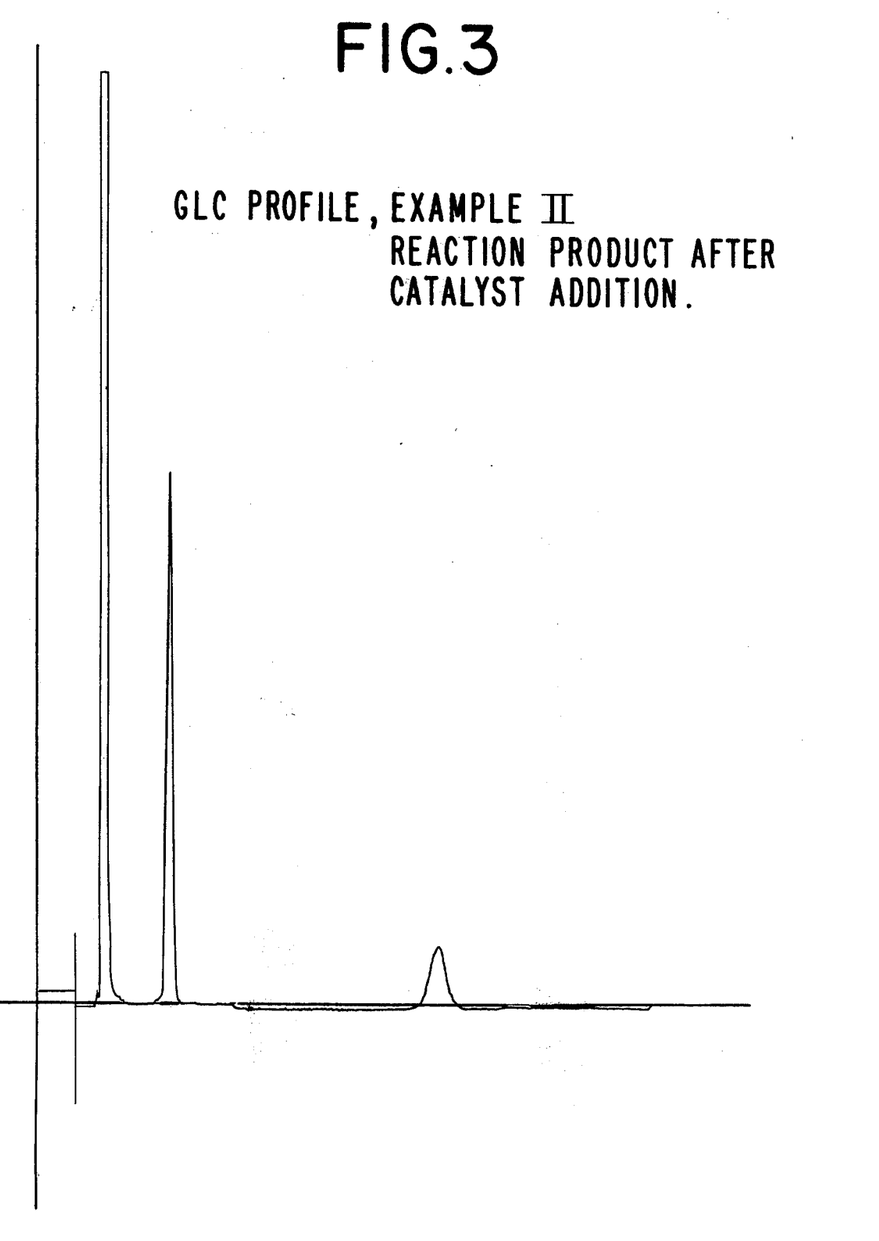
FIG. 3 represents the GLC profile of the reaction product produced according to the Example II immediately subsequent to the addition of Lewis acid catalyst.
Figure 4:
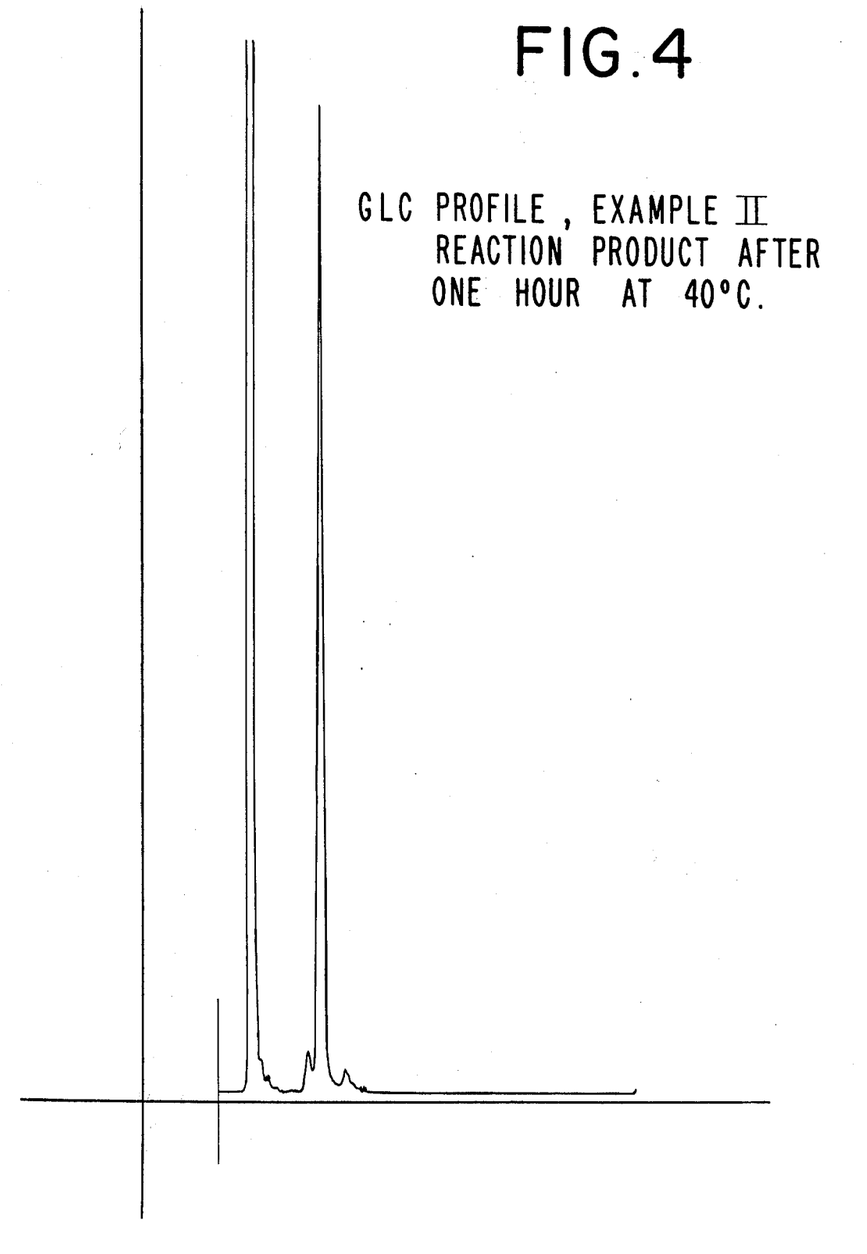
FIG. 4 represents the GLC profile of the reaction product produced according to Example II one hour after raising the temperature of the reaction mass to 40° C.
Figure 5:
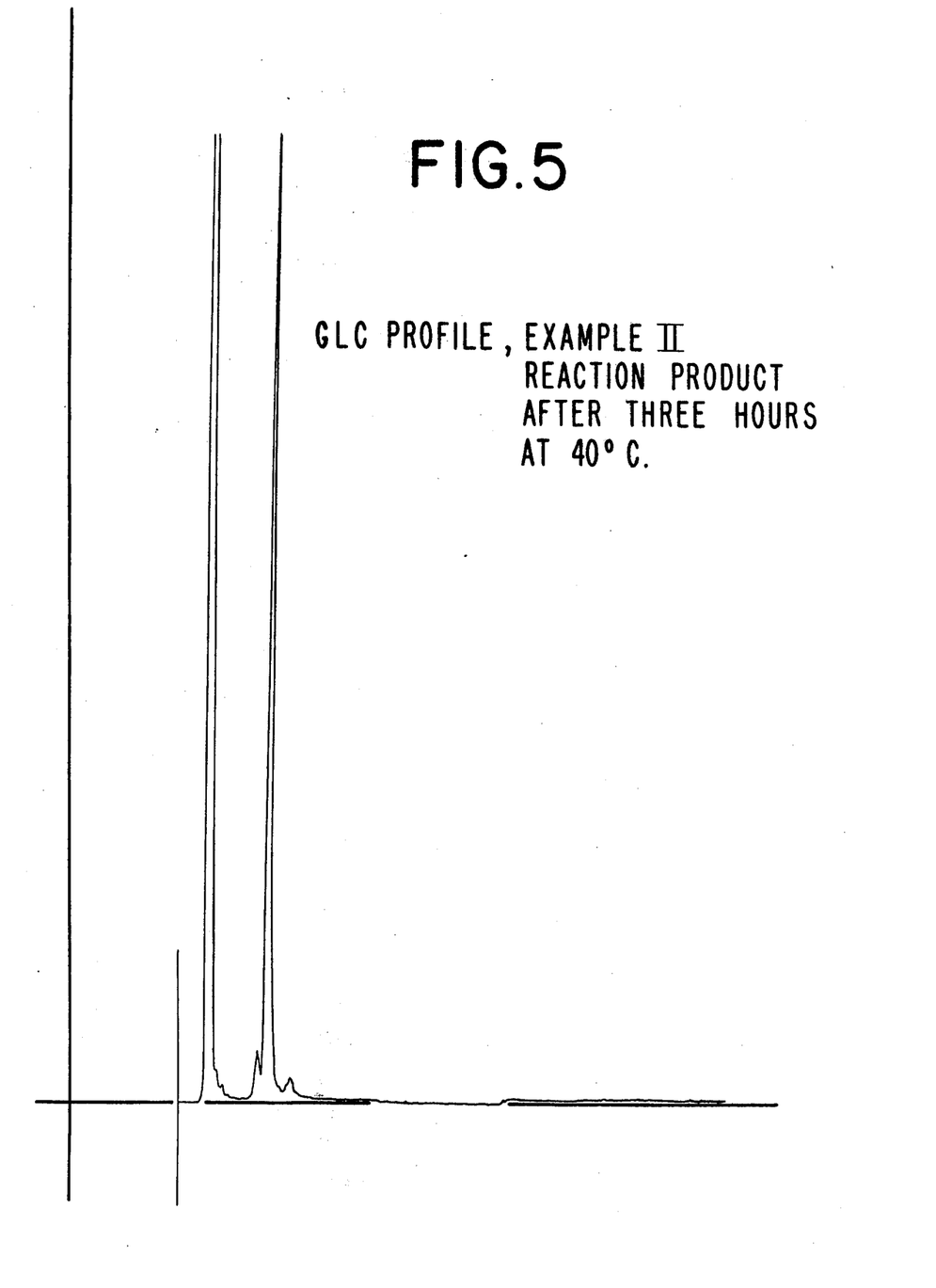
FIG. 5 represents the GLC profile of the reaction product produced according to Example II 3 hours after raising the temperature of the reaction mass to 40° C.

The mixture is heated to 45° C in order to dissolve all of the dimethylhexanediol. The reaction mass is then cooled to 25° C and 1093 grams (8.19 moles) of aluminum trichloride is added while maintaining the reaction mass temperature at 21°–25° C, the addition taking place over a period of 1 hour. FIG. 3 represents the GLC profile of the reaction product immediately subsequent to the additional AlCl₃. Conditions: ⅛ inch × 10 feet 10% SE-30 column operated at 220° C, isothermal). The reaction mass is then heated up to 40° C over a period of 30 minutes and maintained at 40° C, with stirring, for a period of 3 hours. FIG. 4 represents the GLC profile of the reaction product 1 hour after operation at a temperature of 40° C. Conditions: ⅛ inch × 10 feet 10% SE-30 column operated at 220° C, isothermal. FIG. 5 represents the GLC profile of the reaction product 3 hours after operation at a temperature of 40° C. conditions = ⅛ inch × 10 feet 10% SE-30 column operated at 220° C, isothermal. The reaction has substantially gone to completion after operation at 40° C for a period of 1 hour. The reaction mass is then poured into a 22 liter flask containing 500 ml HCl (concentrated), 500 ml water and 3 liters of crushed ice. The resulting mass is then stirred for a period of 30 minutes and the water layer is separated from the organic layer. The organic layer is then washed with 2 liters of water followed by 1 liter of water, followed by 50 ml 50% aqueous sodium hydroxide. 20 ml acetic acid is then added to the mass in order to bring the pH to 6–7. The benzene is then stripped off at atmospheric pressure and the resulting oil is transferred to a small distillation flask and rushed over at 92°–110° C. at a vacuum of 7–10 mm Hg yielding 625 grams of tetrahydrotetramethylnaphthalene (85% yield). NMR, IR and Mass Spectral Analyses yield the information that the resulting product has the structure;

EXAMPLE III

PREPARATION OF 1,1,4,4-TETRAMETHYL TETRAHYDRO NAPHTHALENE FROM 1,1,4,4,5,5,8,8-OCTAMETHYL OCTAHYDRO ANTHRACENE

Reaction:

100 Grams (0.33 moles) of octamethyl octahydro anthracene is dissolved in one kilogram of anhydrous benzene by heating the mixture to 40° C. The resulting solution is then cooled to 25° C and 0.16 moles (21.4 grams) of aluminum chloride is then added in one portion. The reaction mass is then heated to 40° C and maintained there for a period of 1 hour. The reaction mass is then cooled to 25° C and poured into 2 liters of water. The resulting reaction mass exists in two phases; an organic phase and an aqueous phase. The organic phase is washed twice with water. During the second wash, a small portion of 50% sodium hydroxide solution is added in order to adjust the pH to 7. The resulting organic phase is then rushed over at a vapor temperature of 88°–101° C and a vacuum of 6–9 mm Hg. 103 Grams of product is obtained (82% yield based on octamethyloctahydroanthracene). The resulting material having the structure;

is confirmed by NMR, IR and Mass Spectral Analyses.

EXAMPLE IV

PREPARATION OF 1,1,2,3,3-PENTAMETHYLINDANE FROM 1,1,2,3,3,4,4,5,6,6-DECAMETHYL-1,2,3,4,5,6-HEXAHYDRO-s-INDACENE

Reaction:

100 Grams (0.33 moles) of decamethylhexahydro-s-indacene is dissolved in 800 mls of anhydrous benzene by heating the mixture to 40° C. The resulting solution is then cooled to 25° C and 0.1 moles (13.4 grams) of aluminum chloride is then added in one portion. The reaction mass is then cooled to 25° C and poured into 2 liters of water. The resulting aqueous phase is discarded and the organic phase is washed twice with water. A small portion of diluted sodium hydroxide is added to the second wash to adjust the pH to 7–8. The organic phase is rushed over. The product distills at 75°–88° C at 3 mm. 84 Grams of 1,1,2,3,3-pentamethylindane is recovered (68% yield based on charged decamethylhexahydro-s-indacene).

EXAMPLE V

PREPARATION OF 1,1,4,4-TETRAMETHYLTETRAHYDRONAPHTHALENE AND 1,1,4,4,5,5,8,8-OCTAMETHYL-1,2,3,4,5,6,7,8-OCTAHYDROANTHRACENE

Reaction:

Into a 5 liter reaction flask equipped with stirrer, thermometer, reflux condenser, heating mantle, and cooling bath is placed 3000 grams (38.5 moles) of benzene and 400.5 grams (3 moles) of AlCl₃. 272 Grams (1.86 moles) of 2,5-dimethylhexane-2,5-diol is added to the stirred suspension. The mixture is heated to reflux for 2½ hours whereupon the reaction mass is cooled. One liter of water is added thereto, and the lower (aqueous) layer is discarded. The organic solution is washed twice with 1 liter of water. The solvent (benzene) is recovered at atmospheric pressure. Further distillation at 1.5 mm and 74°–79° C vapor temperature yields 144 grams (0.76 moles) of 1,1,4,4-tetramethyltetrahydronaphthalene (38% based on 2,5-dimethylhexane-2,5-diol). The solid material remaining in the still pot is slurried in hexane and filtered to afford 135 grams (0.45 moles) 1,1,4,4,5,5,8,8-octamethyl-1,2,3,4,5,6,7,8-octahydroanthracene as colorless crystals, m.p. 218°–221° C.

What is claimed is:

1. The process for preparing 1,1,4,4-tetramethyltetrahydronaphthalene having the structure:

comprising the step of reacting benzene with 2,5-dimethylhexane-2,5-diol in the presence of an aluminum chloride catalyst (i) in a first stage at a temperature in the range of from about 15° C up to about 25° C and (ii) in a second stage sequentially following said first stage at a temperature in the range of from about 25° C up to the reflux temperature of the reaction mass; said benzene being in molar excess with respect to said diol compound whereby the mole ratio of said benzene:diol compounds in the range of from about 15:1 up to about 50:1.

2. The process of claim 1 wherein the mole ratio of benzene:diol compound is in the range of from 20:1 up to 35:1.

3. The process of claim 2 wherein the mole ratio of diol compound:aluminum chloride is from about 2:1 up to about 5:1.

4. The process of claim 3 wherein the mole ratio of diol compound:aluminum chloride is 2.1:1.

* * * * *